United States Patent
Vredenborg et al.

(10) Patent No.: US 9,797,708 B2
(45) Date of Patent: Oct. 24, 2017

(54) APPARATUS AND METHOD FOR PROFILING A DEPTH OF A SURFACE OF A TARGET OBJECT

(71) Applicant: KONINKLIJKE PHILIPS N.V., Eindhoven (NL)

(72) Inventors: Arno Vredenborg, Eindhoven (NL); Mark Carpaij, Eindhoven (NL); Stephen Gronenborn, Eindhoven (NL); Pavel Pekarski, Eindhoven (NL); Arnd Ritz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 175 days.

(21) Appl. No.: 14/400,580

(22) PCT Filed: May 3, 2013

(86) PCT No.: PCT/IB2013/053534
§ 371 (c)(1),
(2) Date: Nov. 12, 2014

(87) PCT Pub. No.: WO2013/171613
PCT Pub. Date: Nov. 21, 2013

(65) Prior Publication Data
US 2015/0130932 A1    May 14, 2015

(30) Foreign Application Priority Data
May 14, 2012  (EP) .................................... 12167885

(51) Int. Cl.
G01B 11/00    (2006.01)
G01B 11/02    (2006.01)
(Continued)

(52) U.S. Cl.
CPC .......... *G01B 11/026* (2013.01); *A61B 5/1077* (2013.01); *A61B 5/1079* (2013.01);
(Continued)

(58) Field of Classification Search
CPC ...... G01B 11/026; G01B 11/22; A61B 5/1077
(Continued)

(56) References Cited

U.S. PATENT DOCUMENTS

| 5,933,240 A * | 8/1999 | Jurca | G01B 11/026 |
| | | | 356/139.03 |
| 8,475,506 B1 * | 7/2013 | Bendett | A61N 5/0622 |
| | | | 607/88 |

(Continued)

FOREIGN PATENT DOCUMENTS

| DE | 1020080575 A2 | 7/2009 |
| JP | 2006267031 A | 10/2006 |

(Continued)

OTHER PUBLICATIONS

F. Blias, Review of 20 years of range sensor development, Journal of electronic imaging, 13, 231-243, Jan. 2004.

*Primary Examiner* — Jeffery Williams

(57) ABSTRACT

An apparatus (1) for profiling the depth of a surface of a target object (30), having a two-dimensional array of lasers (5), an optical device (15) for projecting a two-dimensional illumination pattern (31) onto an area of the surface of the target object, an image capture device (10) arranged to capture an image of the two-dimensional illumination pattern projected onto the area of the surface of the target object and a processor (25) configured to process the captured image in order to reconstruct a depth profile of the two-dimensional area of the surface of the target object from the image captured by the image capture device.

9 Claims, 7 Drawing Sheets

(51) Int. Cl.
*A61B 5/107* (2006.01)
*A61B 5/00* (2006.01)
*G01B 11/22* (2006.01)
*G01B 11/25* (2006.01)

(52) U.S. Cl.
CPC .............. *A61B 5/444* (2013.01); *G01B 11/22* (2013.01); *G01B 11/2513* (2013.01)

(58) Field of Classification Search
USPC ......................................................... 348/140
See application file for complete search history.

(56) References Cited

U.S. PATENT DOCUMENTS

| | | |
|---|---|---|
| 2003/0198374 A1 | 10/2003 | Hagene |
| 2006/0082882 A1 | 4/2006 | Wang |
| 2008/0238338 A1 | 10/2008 | Latham |
| 2009/0118720 A1* | 5/2009 | Black .................. A61B 18/203 606/9 |
| 2010/0284082 A1 | 11/2010 | Shpunt |
| 2011/0013006 A1 | 1/2011 | Uzenbajakava |
| 2011/0040192 A1 | 2/2011 | Brenner |
| 2011/0058372 A1 | 3/2011 | Lerman |
| 2011/0134114 A1* | 6/2011 | Rais ...................... G06T 7/0057 345/419 |
| 2011/0134436 A1 | 6/2011 | Podoleanu |
| 2011/0279672 A1 | 11/2011 | Chaleff |

FOREIGN PATENT DOCUMENTS

| | | |
|---|---|---|
| JP | 4235684 B1 | 3/2009 |
| JP | 2009517634 A | 4/2009 |
| JP | 2010151958 A | 7/2010 |
| RU | 2050543 C1 | 12/1995 |
| WO | 2007102195 A1 | 9/2007 |
| WO | 2011021139 A2 | 2/2011 |
| WO | 2011070313 A1 | 6/2011 |

* cited by examiner

← 5

← 5 x →

APPARATUS AND METHOD FOR PROFILING A DEPTH OF A SURFACE OF A TARGET OBJECT

This application is the U.S. National Phase application under 35 U.S.C. §371 of International Application No. PCT/IB2013/053534, filed on May 3, 2013, which claims the benefit of European Application No. 12167885.8 filed on May 14, 2012. These applications are hereby incorporated by reference herein.

FIELD OF THE INVENTION

The present invention relates to an apparatus and method for profiling a depth of a surface of a target object.

BACKGROUND OF THE INVENTION

Techniques for generating 3D digital data are an active area of research, for example to allow for gesture control and recording 3D scenes. There are three main range finding techniques which are interferometry, triangulation and time-of-flight imaging. The latter can be used for larger depth ranges, while triangulation is better for close ranges. to achieve a high resolution, interferometry-based methods may be used. Triangulation is a known technique wherein active lighting and an image recording device are used. Active lighting techniques make use of a specific light pattern which is projected onto a target object. Subsequently, the distortions of the detected light pattern can be used to reconstruct the depth profile.

Non-contact methods of depth profiling of surfaces, for example skin, may be required to detect and quantify surface quality, like wrinkles and fine lines. A non-contact method for close range measurement may be required where contact between the depth profiling apparatus and the surface could deform the depth profile of the surface to be scanned and lead to a false measurement. In the medical domain, depth profiling could be used to scan moles (melanocytic nevus) in the home environment and to follow the growth of the mole over time. In another field, one would possibly like to scan the surface relief structure of leaves. Depth profiling may be of interest with respect to features on the order of micrometers or greater.

Laser line scanners are known which profile 3D objects in process lines of industry whereby a laser line is imaged by an optical diffractive element and is moved across the surface of the target object. However, these require accurate motion and/or possibly tracking of either the laser line or the object to obtain 3D data of the object under investigation. Speckle noise from the laser is a limiting factor.

Another method is to use a light projector device, but these are relatively large and expensive. Moreover, projector devices are typically used for larger object like complete faces with lower depth resolution of several millimeters.

Another way of producing a particular, often complex, light pattern is by use of multiple diffractive optical elements. However, design of the diffractive element is not straightforward. Moreover further miniaturization increases the demands on the design of the diffractive optical element, with a necessity for smaller structure. There is a limit to size of the smallest structure that can be made by cost-effective means in transparent glass or plastic plate. Reference is made to US 2011/013006 A1; US 2011/040192 A1 and US 2009/118720.

SUMMARY OF THE INVENTION

The present invention provides an apparatus for profiling a depth of a surface of a target object, the apparatus comprising a first light source comprising a two-dimensional array of lasers, an optical device for projecting a two-dimensional multiline illumination pattern onto an area of the surface of the target object, an image capture device arranged to capture an image of the two-dimensional illumination pattern projected onto the area of the surface of the target object and a processor configured to process the captured image in order to reconstruct a depth profile of the two-dimensional area of the surface of the target object from the image captured by the image capture device, wherein the two dimensional array comprises a plurality of rows wherein at least one row is laterally offset with respect to an adjacent row.

The present invention may provide that the two-dimensional array of lasers comprises at least two lasers having different shapes.

The present invention may provide that the two-dimensional array is configured to be switched between a homogeneous illumination mode and a structured illumination mode.

The present invention may provide means for determining distance between the two-dimensional array and the surface of a target object.

The present invention may provide that the means for determining distance between the two-dimensional array and the surface of a target object comprises a second light source inclined at a predetermined angle relative to the first light source, wherein the second light source is configured to project a second illumination pattern onto the surface of the target object and the image capture device is configured to capture an image of the second illumination pattern, and wherein the processor is further configured to process the captured image of the second illumination pattern and determine a distance between the first active light source and the surface of the target object based on the predetermined angle and the captured image of the second illumination pattern.

The present invention may provide that the two-dimensional array of lasers comprises vertical cavity surface emitting lasers.

The present invention provides a method of profiling a depth of a surface of a target object, the method comprising projecting a two-dimensional multiline illumination pattern from a first light source comprising a two-dimensional array of lasers onto an area of the surface of the target object, capturing an image of the illumination pattern and processing the captured image in order to reconstruct a depth profile of the area of the surface of the target object from the image captured by the image capture device, wherein the two dimensional array comprises a plurality of rows wherein at least one row is laterally offset with respect to an adjacent row.

The present invention may provide switching the two dimensional array between a homogeneous illumination mode and a structured illumination mode.

The present invention may provide determining a distance between the two-dimensional array and the surface of the target object.

The present invention may provide that determining a distance between the two-dimensional array and the surface of a target object comprises directing a second light source towards the target object, the second light source oriented at a predetermined angle to the first light source, projecting, from the second light source, a second illumination pattern onto the surface of the target object, capturing an image of the second illumination pattern, processing the captured image of the second illumination pattern, and determining the distance between the first active light source and the surface of the target object based on the predetermined angle and the captured image of the second illumination pattern.

The present invention may provide a computer readable storage medium arranged to store computer program instructions that, when executed by a processor, perform the method provided by the invention.

BRIEF DESCRIPTION OF THE DRAWINGS

So that the present invention may be fully understood, embodiments thereof will be described by way of example only with reference to the accompanying drawings in which.

DETAILED DESCRIPTION

Figure 1:
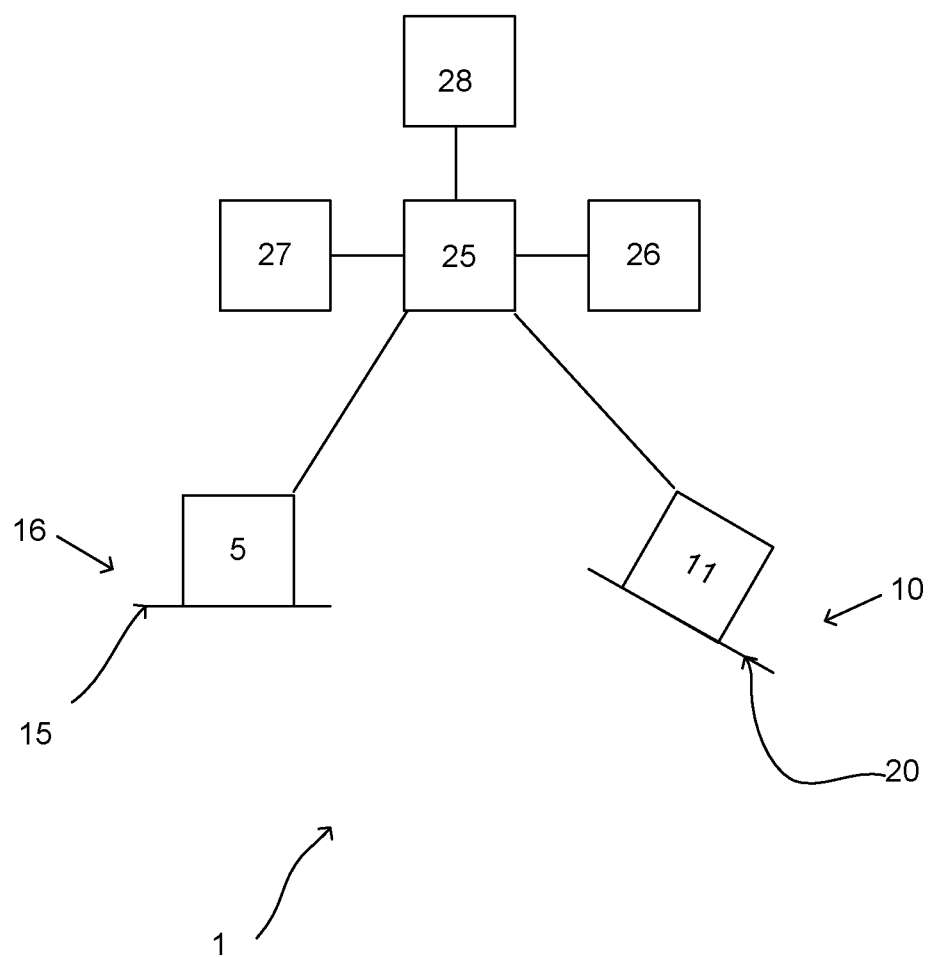
FIG. 1 is a schematic representation of a depth profiling apparatus according to an embodiment of the present invention.

FIG. 1 shows a depth profiling apparatus 1 comprising a two dimensional laser array 5, an image capture device 10 such as a CCD or CMOS camera and a first lens 15 coupled to the laser array 5. The image capture device 10 may comprise an image capture array and a second lens 20 to focus an image captured by the image capture device 10. The depth profiling apparatus 1 may further comprise a processor 25 to control the depth profiling apparatus 1 and to process images captured by the image capture device 10. The depth profiling apparatus 1 may further comprise a memory 26 for storing software used by the processor to control the depth profiling apparatus 1 and to process captured images. The depth profiling apparatus 1 may further comprise a power source 27 such as a battery or a mains connection and may comprise a user interface 28 having an output unit such as a display screen and/or an input unit such as a keyboard.

Figure 2A:
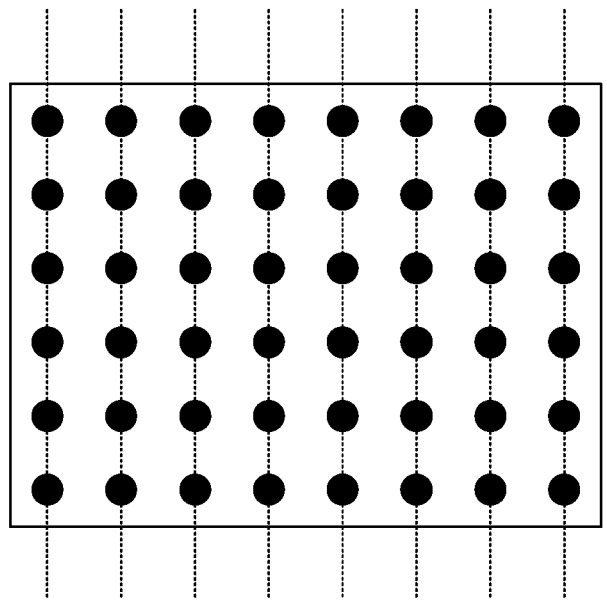
FIGS. 2A and 2B are plan views of a laser array according to respective embodiments of the present invention.
Figure 2B:
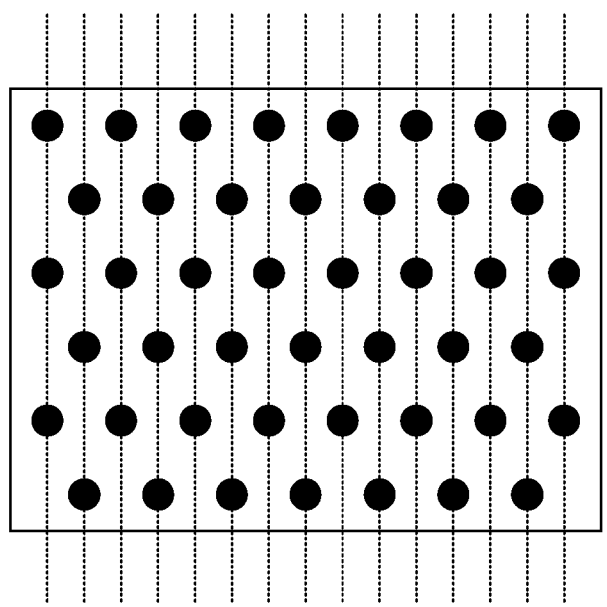

FIGS. 2A and 2B show a laser array 5 in plan view according to two exemplary embodiments.

FIG. 2A shows a rectangular laser array 5 where each laser ($1^{st}$, $2^{nd}$, $3^{rd}$ etc) on a particular row of the laser array 5 has the same x-axis coordinate as a respective laser ($1^{st}$, $2^{nd}$, $3^{rd}$ etc) on the preceding and following rows, where the x-axis is the row direction as shown by the arrow at the bottom of FIG. 2B.

FIG. 2B shows a laser array 5 where successive rows are displaced by a certain distance along the x-axis compared with a preceding row.

The laser array 5 may be an array of vertical cavity surface emitting lasers (hereinafter, VCSELs). The use of VCSELs in the laser array 5 is advantageous due to their high efficiency, low current threshold current and high modulation bandwidths. Furthermore, using an array of VCSELs has cost advantages due to the vertical emission of the lasers which allows for straightforward processing and wafer scale testing as well as integration of wafer scale optics. The layout of multiple VCSELs in an array such as the laser array 5 can be controlled by one lithographic step during manufacture, which allows a high freedom of choice with respect to shape, size and density over the array surface area.

The laser array 5 may have an area of approximately 1 square millimeter (hereinafter, sq mm) or smaller in preferred embodiments. Having an array of lasers is advantageous because of the small dimensions that may be achieved which reduces the cost of manufacture. Furthermore, using a cylindrical lens to image the array in one dimension (i.e. in lines) is a simpler arrangement than using more complex optical devices.

The laser array 5 may comprise between 5 and 50 rows, each row comprising between 10 and 50 lasers. Successive rows may be shifted in the x-direction with respect to the preceding row, substantially as shown in FIG. 2B.

Each of the lasers within the laser array 5 may have a diameter between approximately 1 micrometer and approximately 25 micrometers (hereinafter, microns) and may be separated by approximately 25 microns. For example, an array comprising 18 rows may be employed, with each row comprising 25 lasers, each with a diameter of approximately 5 microns and a separation of approximately 25 microns between each laser. As shown in FIG. 2B, each successive row may be shifted in the x-direction by half the separation between each laser. In the above example, the shift may be approximately 12.5 microns. As such, the position in the x-direction of successive lasers (i.e. the $1^{st}$, $2^{nd}$, $3^{rd}$, ...) in a row corresponds to the position in the x-direction of successive lasers in alternate rows.

The first lens 15, shown in FIG. 1 may be a cylindrical lens which is placed in front of the array 5. Cylindrical lenses may be used to focus light passing there through onto a line. The first lens 15 may be plano-convex or convex-convex although a Fresnel lens or single diffractive optical element may be used instead. The laser array 5 and first lens 15 together form a laser projector 16.

Figure 3:
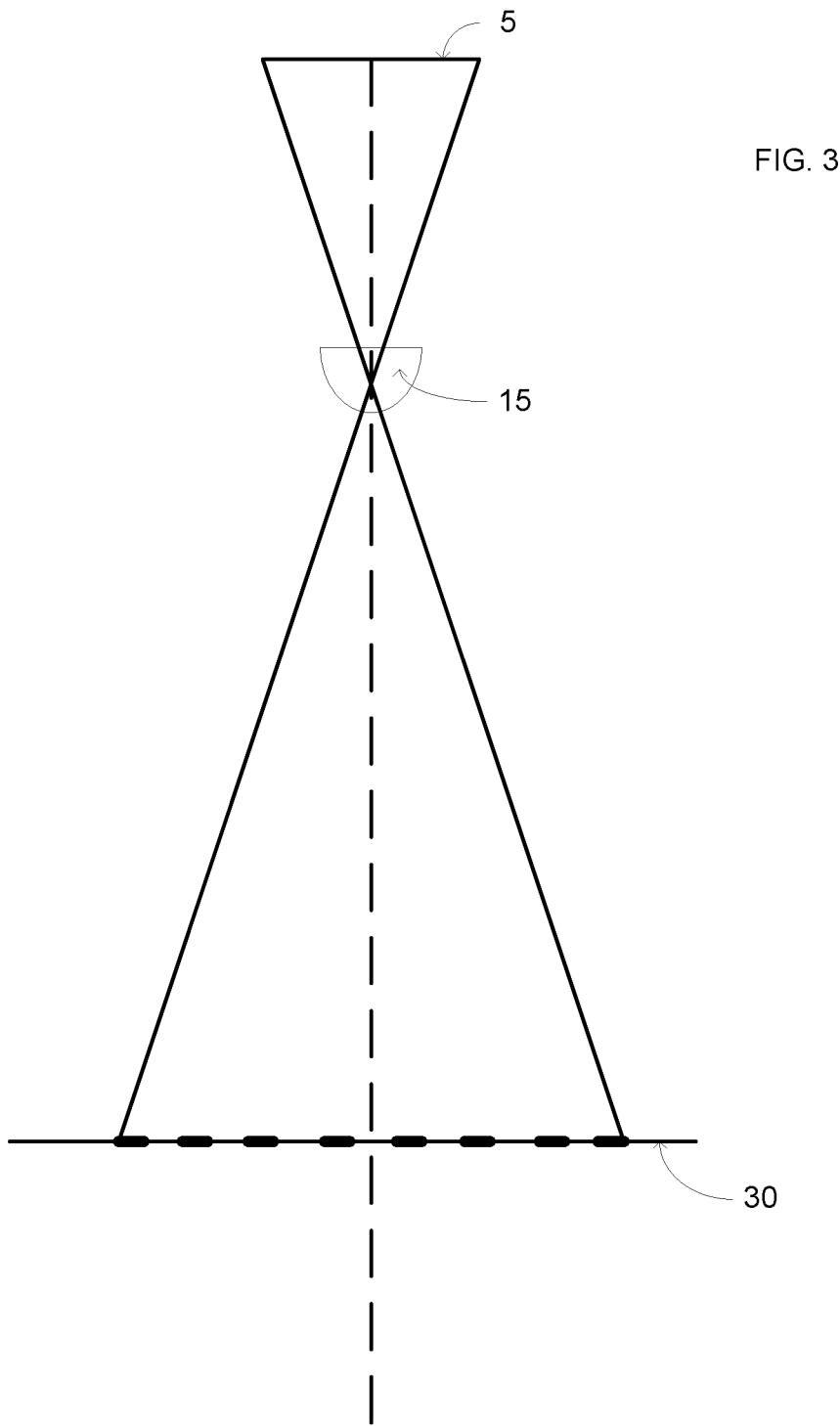
FIG. 3 is a side-on view diagram showing an embodiment of the present invention.

FIG. 3 shows the laser array 5, first lens 15 and a target object 30 having a two-dimensional illumination pattern 31 projected thereon according to one embodiment. In this embodiment the first lens 15 is a cylindrical lens and the two-dimensional illumination pattern 31 is a multiline pattern. The number of lines projected depends on the arrangement of the laser array 5.

For example, a rectangular array such as that shown in FIG. 2A will project eight lines equal to the number of lasers in each row. An array such as that shown in FIG. 2B will generate 15 lines 31. In the above described example, where there are 25 lasers in a row and each successive row is shifted in the x-direction by a distance equal to half the inter-laser separation (similar to the arrangement shown in FIG. 2B) then 50 lines will be projected onto the surface of the target object 30.

Embodiments of the invention may have successive rows of lasers shifted in the x-direction with respect to the preceding row by a varying amount. Each laser in the laser array 5 may therefore have a unique position in the x-direction thereby increasing the number of laser lines projected onto the surface of the target object 30 up to a number equal to the number of lasers in the laser array 5.

Figures 4A, 4B:
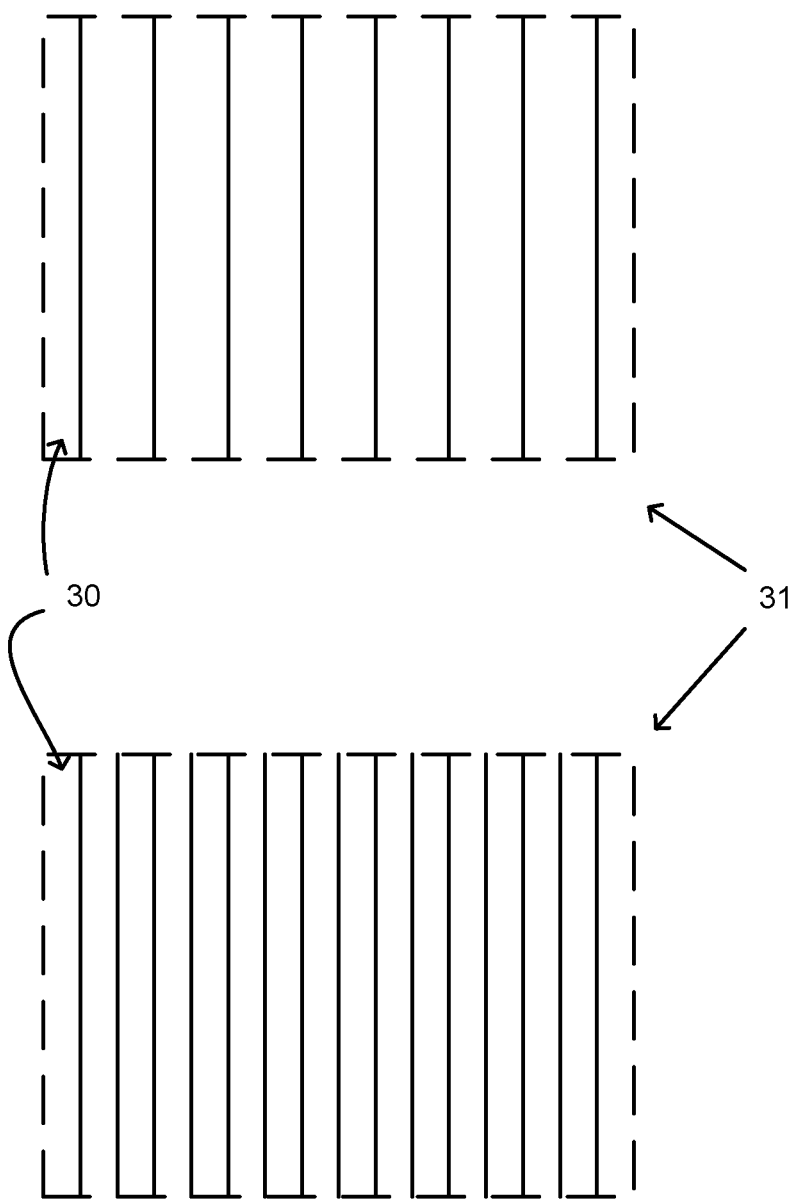
FIGS. 4A and 4B are plan views of illumination patterns according to respective embodiments of the present invention.

FIG. 4A shows an illumination pattern 31 obtained from the laser array 5 shown in FIG. 2A and FIG. 2B shows an illumination pattern 31 obtained from the laser array 5 shown in FIG. 2B in plan view when using a cylindrical first lens 15.

Figure 5:
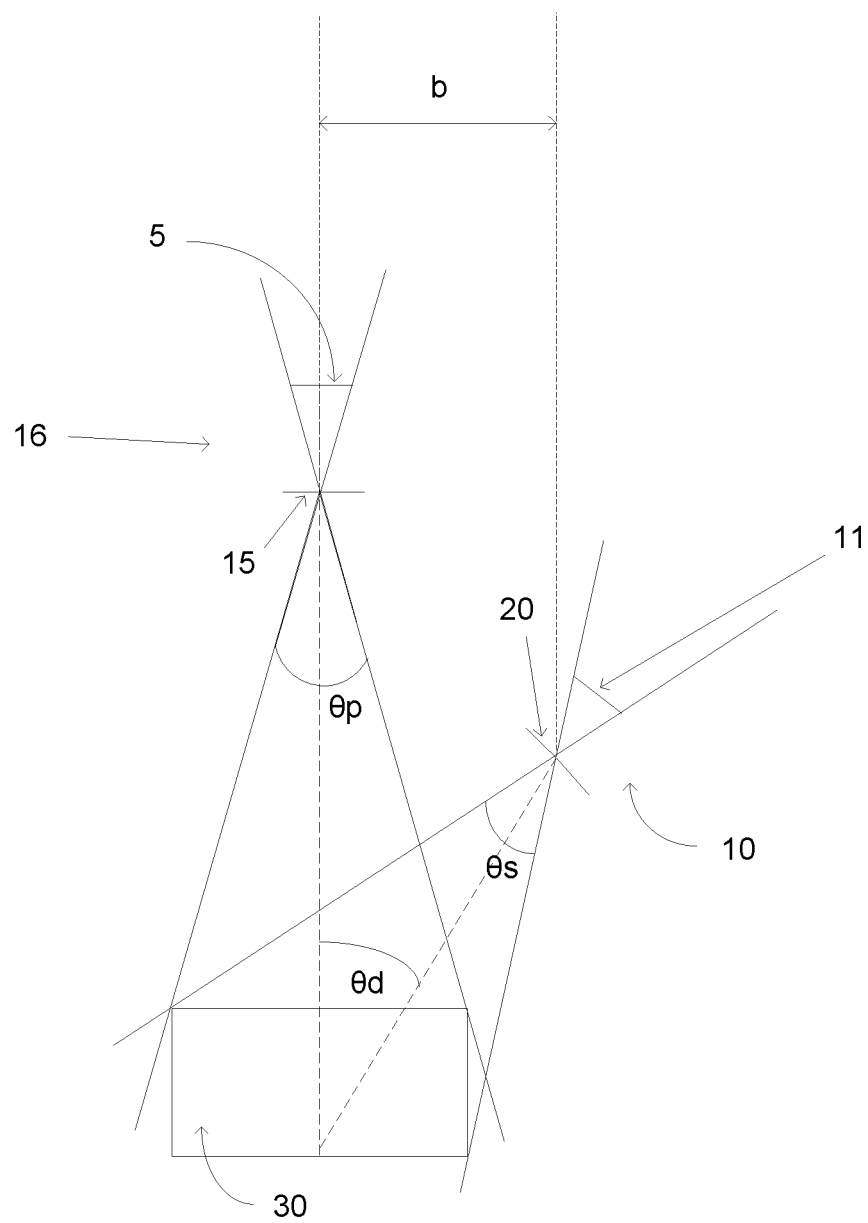
FIG. 5 is a diagram of an embodiment of the present invention.

FIG. 5 is a diagram showing the laser projector 16 and image capture device 10 arranged to profile a target object 30. The image capture device 10 is oriented at an angle θd relative to the laser projector 16. The laser projector 16 has an opening angle θp and the image capture device 10 has a field of view of θs.

The first lens 15 may have a focal length of the order of several millimeters and the laser projector 16 may have an opening angle θp of between approximately 5 and approximately 45 degrees.

The laser array 5 may be positioned relative to the first lens 15 so that it is in or out of focus. If the laser array 5 is located a distance from the first lens 15 equal to the focal length then the laser array 5 is imaged at infinity and has a maximum depth of focus.

In embodiments of the invention, the first lens 15 may have a focal length of 3 mm and the laser array 5 may be located at a distance 3.5 mm away from the first lens 15. An image of the laser array 5 is thereby created at a distance of 21 mm from the laser array 5, the image being magnified by a factor of 6. This leads to an illumination area of the order of 6×6 mm. In this embodiment of the invention, the laser projector 16 has an opening angle θp of approximately 17 degrees. The opening angle θp may be increased by using a first lens 15 having a shorter focal length.

In use, a two-dimensional illumination pattern comprising a plurality of lines may be projected onto the surface of the target object 30 by the laser projector 16 as described above. Diffuse scattering or reflection of the illumination pattern occurs and the illumination pattern on the surface of the target object 30 is captured by the image capture device 10.

The image capture device 10 is arranged so that it has a base distance b as shown in FIG. 4 of between approximately 5 mm and approximately 50 mm. In some embodiments of the invention, the angle θd may be between approximately 25 and approximately 45 degrees. However, the angle θd depends on the depth range and area of the surface of the target object 30.

The image capture device 10 captures and records an image of the surface of the target object 30 and the two-dimensional illumination pattern projected thereon by the laser projector 16. The illumination pattern is distorted by the depth profile of the surface of the target object 30. The processor 25, using software stored in the memory 26, reconstructs the depth profile of the surface of the target object 30 onto which the illumination pattern has been projected. Suitable depth profile reconstruction software will be apparent to those skilled in the art. Depth profile information may be output via the user interface 28.

Advantageously, the depth of a two-dimensional area of the surface may be profiled without sweeping the illumination pattern across the target object 30. Several images of the surface of the target object 30 captured by the image capture device 10 may be combined to obtain a depth profile of a large area of the surface since the software is configured to recognize surface features which are common to several captured images. As such, it is not necessary to track the movement of the apparatus 1 when combining several images.

In the embodiments of the invention hereinbefore described, the illumination pattern projected onto the surface of the target object 30 comprises a plurality of lines. However, in alternative embodiments of the present invention the illumination pattern may have a different structure. For example, different shapes may be projected onto the surface of the target object 30.

In preferred embodiments of the present invention the distance between the laser array 5 and the surface of the target object 30 is determined. Determining the distance between the laser array 5 and the surface of the target object 30 enables a magnification factor of the illumination pattern to be calculated and allows the apparatus 1 to be operated in a non-static or hand-held mode.

The distance between the laser array 5 and the surface of the target object 30 may be calculated using triangulation of the illumination pattern projected onto the surface of the target object 30. Triangulation using a projected pattern is a conventional method with which the person skilled in the art will be familiar. Alternatively, a time of flight method may be employed, wherein a laser pulse is projected onto the surface of the target object 30 and the time taken for the scattered or reflected laser to be detected is measured. The distance may then be calculated in a manner familiar to those skilled in the art. The distance between the laser array 5 and the surface of the target object 30 may also be calculated using known methods based on interferometry which will be apparent to those skilled in the art.

Figure 6:
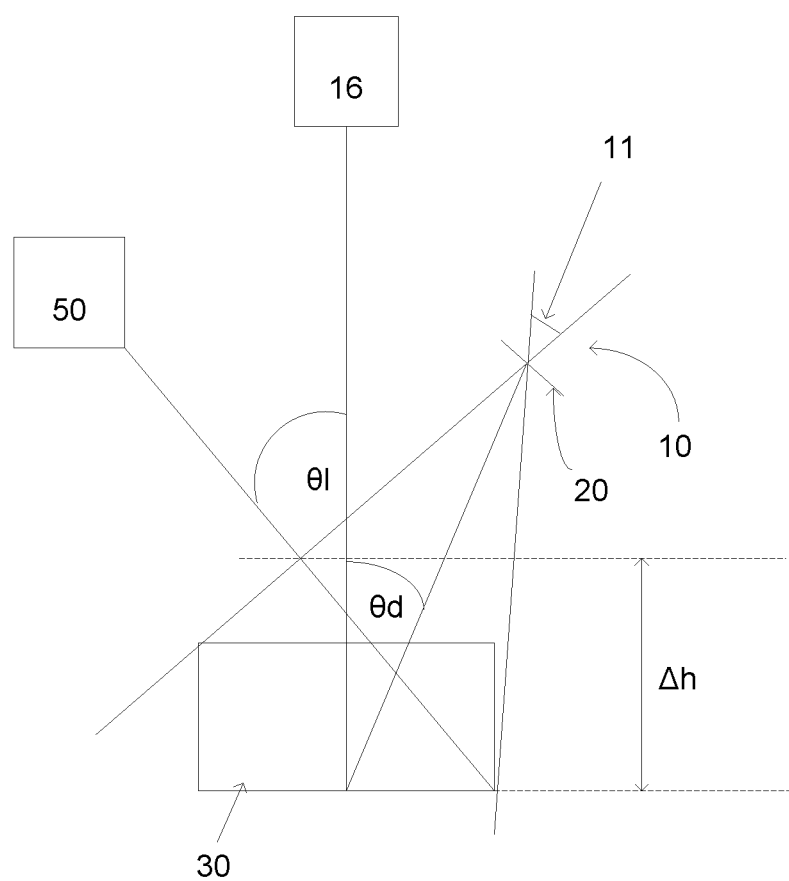
FIG. 6 is a diagram of an embodiment of the present invention.

In yet another embodiment, the depth profiling apparatus may comprise a second light source 50. The distance between the laser array 5 and the surface of the target object 30 may be determined by using the second light source 50 as shown in FIG. 6. The second laser light source 50 may be a second array of lasers or alternatively, a single laser. The laser used in the second light source 50 may be a VCSEL.

The second laser light source 50 is collimated and positioned at an angle $\theta_1$ with respect to the laser projector 16 and a second illumination pattern, independent of the illumination pattern obtained from the laser array 5, is projected onto the surface of the target object 30. The second illumination pattern may then be captured using the image capture device 10. The position of the second illumination pattern on the surface of the target object 30 varies with the distance between the apparatus 1 and the target object 30. The position of the second illumination pattern and the angle $\theta_1$ may be used by the processor 25 to determine the distance using suitable software stored in the memory 26.

As shown in FIG. 6, only a certain depth range Δh can be detected by the image capture device 10. The apparatus 1 may be provided with an audible alarm (not shown) controlled by the processor 25. The processor 25 may be configured to actuate the audible alarm when the apparatus 1 is at a distance from the target object 30 which allows the surface of the target object 30 to be profiled.

In certain embodiments, separate regions of the laser array 5 may be individually addressed so that a time-varying illumination pattern may be obtained which can improve the accuracy of the triangulation-based distance determination hereinbefore described. By pulsing operation of the laser array 5, the duty cycle of the laser array 5 may be reduced. Operation of the laser array 5 may be synchronized with that of the image capture device 10 to reduce power consumption.

In certain embodiments the shape of individual lasers may be varied to produce any two-dimensional shape using a lithographic mask for example circles, squares or trapeziums. An illumination pattern may therefore be produced combining different shapes projected onto the surface of the target object 30. An advantage of such embodiments is that the image processing algorithms used by the processor 25 may be simplified since individual lasers may be identified based on the projected illumination pattern.

In certain embodiments, the laser array 5 may include individual VCSELs having different shapes to produce a different illumination pattern from those hereinbefore described. Such an illumination pattern has the advantage that individual VCSELs within the array 5 may be identified based on the illumination pattern observed. Since lasers of different shapes may be operated in parallel, variations in the active area of the individual lasers may be limited to the range of +/−10%.

Figure 7:
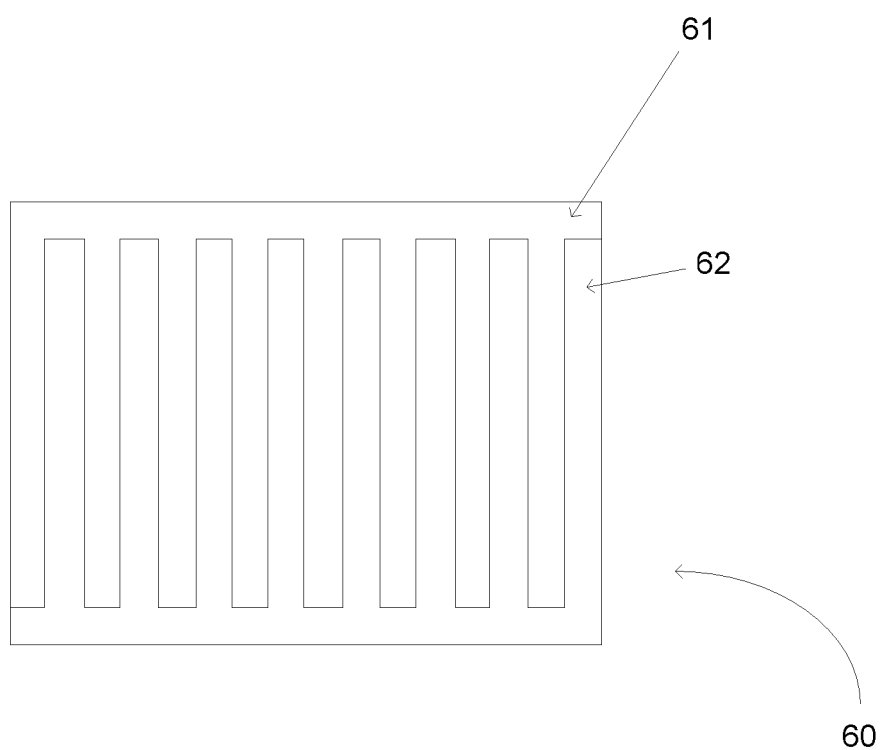
FIG. 7 is a plan view of a chip supporting a laser array according to an embodiment of the present invention.

The laser array 5 is supported by a chip. FIG. 7 shows a chip 60 according to one embodiment. The chip 60 comprises first and second chip regions 61, 62 which may be contacted separately to a power supply to allow electronic switching between homogenous illumination and structured illumination. If all lasers are operated, an illumination pattern having a rectangular homogeneous intensity pattern is obtained. By addressing only one of the chip regions 61, 62, every alternate row is illuminated resulting in a striped pattern, to allow measurement of the distance between the array 5 and the surface of the target object 30. It will be appreciated by those skilled in the art that more than two areas of the chip can be addressed using known methods.

The laser array 5 may be arranged so that individuals lasers may be switched on and off This feature has the advantage of reducing ambiguity between features of the illumination pattern captured by the image capture device 10.

In certain further embodiments, a diffraction grating may be added to each individual laser. The addition of a diffraction grating is a wafer-scale process. The diffraction grating may stabilize the polarization of the emitted laser light.

The image capture device may be provided with a polarizer to decrease the amount of ambient light captured. Ambient light is noise with respect to the captured illumination pattern which is of interest. The polarization direction of individual lasers in the array 5 may be varied. In this way, two or more illumination patterns may be obtained from the array, and detected by a camera with correct polarizer's. This would avoid additional electronics to have to switch the individual lasers on or off and would advantageously allow the use of time-of-flight and triangulation methods at the same time.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived there from.

Other modifications and variations falling within the scope of the claims hereinafter will be evident to those skilled in the art.

The invention claimed is:

1. A hand-held depth profiling apparatus for profiling a depth of a surface of a target object, the apparatus comprising:
    a first light source comprising a two-dimensional array of laser, wherein the first light source has an opening angle $\theta p$ substantially between 5 and 45 degrees, and wherein the opening angle $\theta p$ is inversely correlated to a focal length of the first light source;
    an optical device for projecting a two-dimensional multiline illumination pattern onto an area of the surface of the target object, wherein the optical device has a focal length on the order of several millimeters and wherein the two-dimensional multiline illumination pattern is distorted by a depth profile of the surface of the target object;
    an image capture device arranged to capture an image of the two-dimensional illumination pattern projected onto the area of the surface of the target object, wherein the image capture device is oriented at an angle $\theta d$ relative to the first light source, and wherein the image capture device has a field of view of $\theta s$, wherein the angle $\theta d$ depends on a depth range and area of the surface of the target object;
    a processor configured to process the captured image in order to reconstruct the distorted depth profile of a two-dimensional area of the surface of the target object from the image captured by the image capture device, and
    means for determining distance between the apparatus and the surface of the target object,
    wherein the two dimensional array comprises a plurality of rows, wherein at least one row is laterally offset with respect to an adjacent row.

2. An apparatus according to claim 1, wherein the two-dimensional array of lasers comprises at least two lasers having different shapes.

3. An apparatus according to claim 1, wherein the two-dimensional array is configured to be switched between a homogeneous illumination mode and a structured illumination mode.

4. An apparatus according to claim 1, wherein the means for determining distance between the two-dimensional array and the surface of a target object comprises a second light source inclined at a predetermined angle relative to the first light source,
    wherein the second light source is configured to project a second illumination pattern onto the surface of the target object and the image capture device is configured to capture an image of the second illumination pattern, and
    wherein the processor is further configured to process the captured image of the second illumination pattern and determine a distance between the first light source and the surface of the target object based on the predetermined angle and the captured image of the second illumination pattern.

5. An apparatus according to claim 1, wherein the two-dimensional array of lasers comprises vertical cavity surface emitting lasers.

6. A method of profiling a depth of a surface of a target object using a hand-held apparatus, the method comprising:
    projecting a two-dimensional multiline illumination pattern from a first light source comprising a two-dimensional array of lasers onto an area of the surface of the target object, wherein the first light source has an opening angle $\theta p$ substantially between 5 and 45 degrees, and wherein the opening angle $\theta p$ is inversely correlated to a focal length of the first light source;
    capturing an image of the illumination pattern on an image capture device, wherein the image capture device is oriented at an angle $\theta d$ relative to the first light source, and wherein the image capture device has a field of view of θs, wherein the angle θd depends on a depth range and area of the surface of the target object;

processing the captured image in order to reconstruct a depth profile of the area of the surface of the target object from the image captured by the image capture device; and determining a distance between the hand-held apparatus and the surface of the target object, wherein the two dimensional array comprises a plurality of rows wherein at least one row is laterally offset with respect to an adjacent row.

7. A method according to claim 6, further comprising switching the two dimensional array between a homogeneous illumination mode and a structured illumination mode.

8. A method according to claim 6, wherein determining a distance between the two-dimensional array and the surface of a target object comprises:

directing a second light source towards the target object, the second light source oriented at a predetermined angle to the first light source, projecting, from the second light source, a second illumination pattern onto the surface of the target object, capturing an image of the second illumination pattern, processing the captured image of the second illumination pattern, and determining the distance between the first light source and the surface of the target object based on the predetermined angle and the captured image of the second illumination pattern.

9. A non-transitory computer readable storage medium, having stored thereon instructions that when executed by a processor cause processing circuitry of a hand-held depth profiling apparatus to project a two-dimensional multiline illumination pattern from a first light source comprising a two-dimensional array of lasers onto an area of the surface of the target object, wherein the first light source has an opening angle θp substantially between 5 and 45 degrees, and wherein the opening angle θp is inversely correlated to a focal length of the first light source;

capture an image of the illumination pattern;

process the captured image by an image capture device in order to reconstruct a depth profile of the area of the surface of the target object from the image captured by the image capture device, wherein the image capture device is oriented at an angle θd relative to the first light source, and wherein the image capture device has a field of view of θs, wherein the angle θd depends on a depth range and area of the surface of the target object; and determine a distance between the hand-held apparatus and the surface of the target object, wherein the two dimensional array comprises a plurality of rows wherein at least one row is laterally offset with respect to an adjacent row.

* * * * *